United States Patent
Holland

(10) Patent No.: US 10,155,757 B2
(45) Date of Patent: Dec. 18, 2018

(54) CRYSTALLINE FORM OF A JAK3 KINASE INHIBITOR

(71) Applicant: VECTURA LIMITED, Chippenham Wiltshire (GB)

(72) Inventor: Joanne Holland, Chippenham (GB)

(73) Assignee: Vectura Limited, Chippenham, Wiltshire (GB)

( * ) Notice: Subject to any disclaimer, the term of this patent is extended or adjusted under 35 U.S.C. 154(b) by 0 days.

(21) Appl. No.: 15/555,590

(22) PCT Filed: Feb. 29, 2016

(86) PCT No.: PCT/EP2016/054237
§ 371 (c)(1),
(2) Date: Sep. 5, 2017

(87) PCT Pub. No.: WO2016/142201
PCT Pub. Date: Sep. 15, 2016

(65) Prior Publication Data
US 2018/0044336 A1  Feb. 15, 2018

(30) Foreign Application Priority Data

Mar. 10, 2015  (EP) .................................... 15158443

(51) Int. Cl.
*C07D 471/04* (2006.01)
*C07C 57/145* (2006.01)

(52) U.S. Cl.
CPC .......... *C07D 471/04* (2013.01); *C07C 57/145* (2013.01)

(58) Field of Classification Search
CPC ............................ C07D 471/04; C07C 57/145
USPC ........................................................ 514/283
See application file for complete search history.

(56) References Cited

FOREIGN PATENT DOCUMENTS

WO   WO 2011/051452 A1   5/2011

OTHER PUBLICATIONS

Stahl, Peter Heinrich et al., "Handbook of Pharmaceutical Salts, Table 1, Acids: Alphabetical Order," Handbook of Pharmaceutical Salts: Properties, Selection, and Use, pp. 334-335 (2002).
International Search Report for International Application No. PCT/EP2016/054237, dated Apr. 13, 2016.
Written Opinion of the International Searching Authority for International Application No. PCT/EP2016/054237.

*Primary Examiner* — Kristin A Vajda
(74) *Attorney, Agent, or Firm* — Finnegan, Henderson, Farabow, Garrett & Dunner, L.L.P.

(57) ABSTRACT

The invention relates to novel co-crystals of a drug substance and their use to treat respiratory diseases such as asthma and COPD.

13 Claims, 6 Drawing Sheets

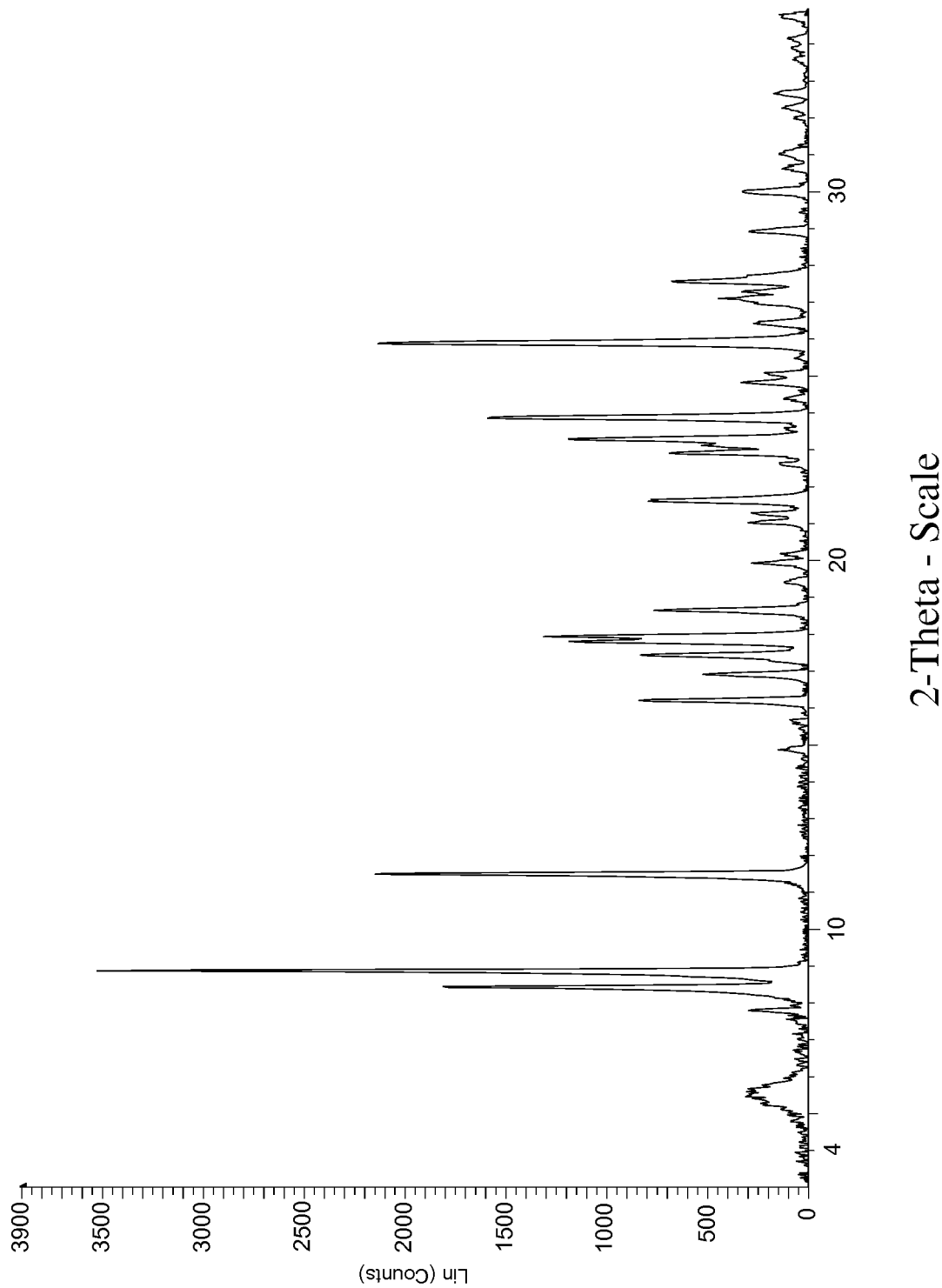
Fig. 1: XRPD Pattern for the 1:1 VR588 Maleic Acid Co-crystal

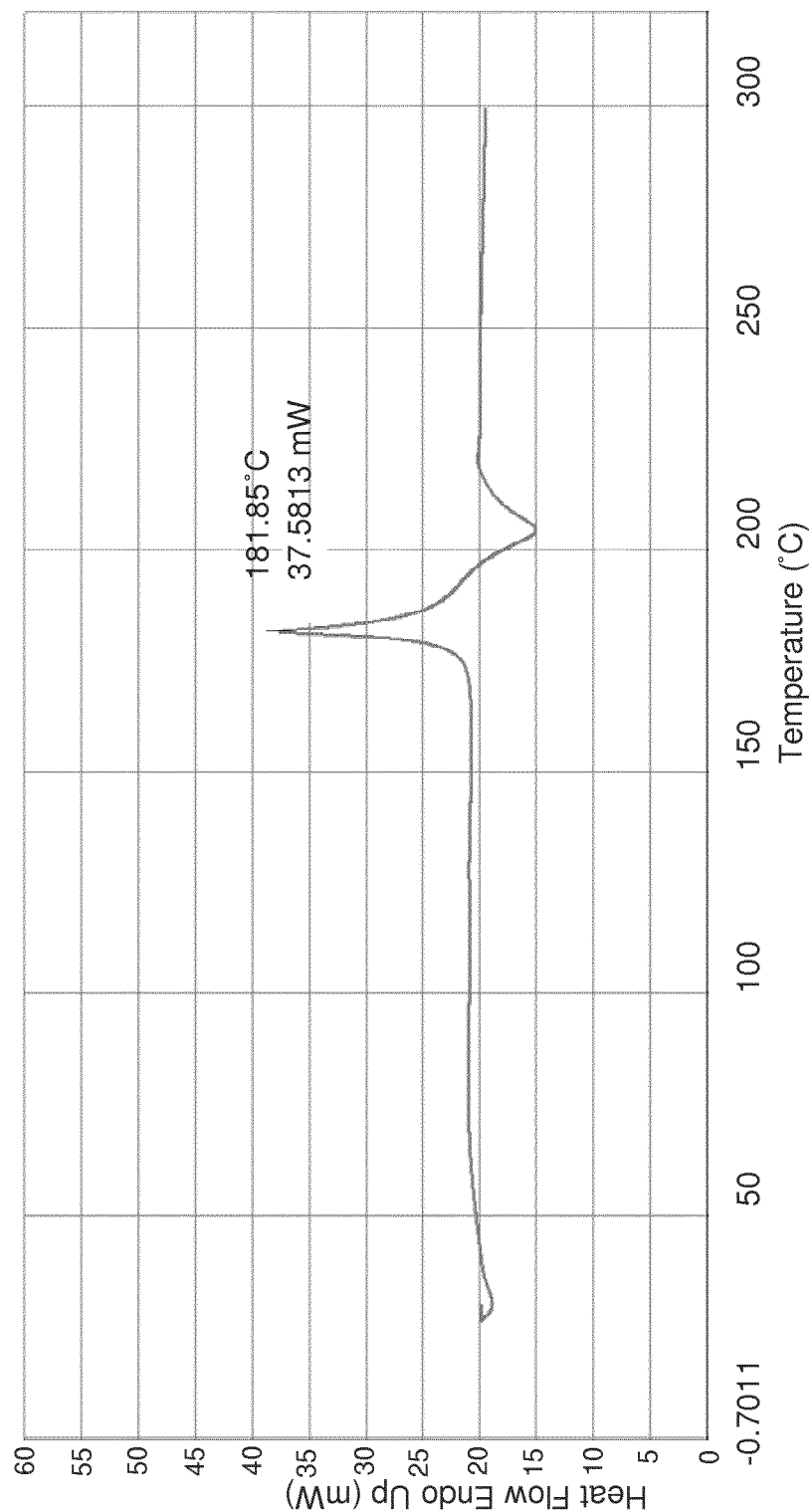
Fig.2: DSC Trace for the 1:1 VR588 Maleic Acid Cocrystal

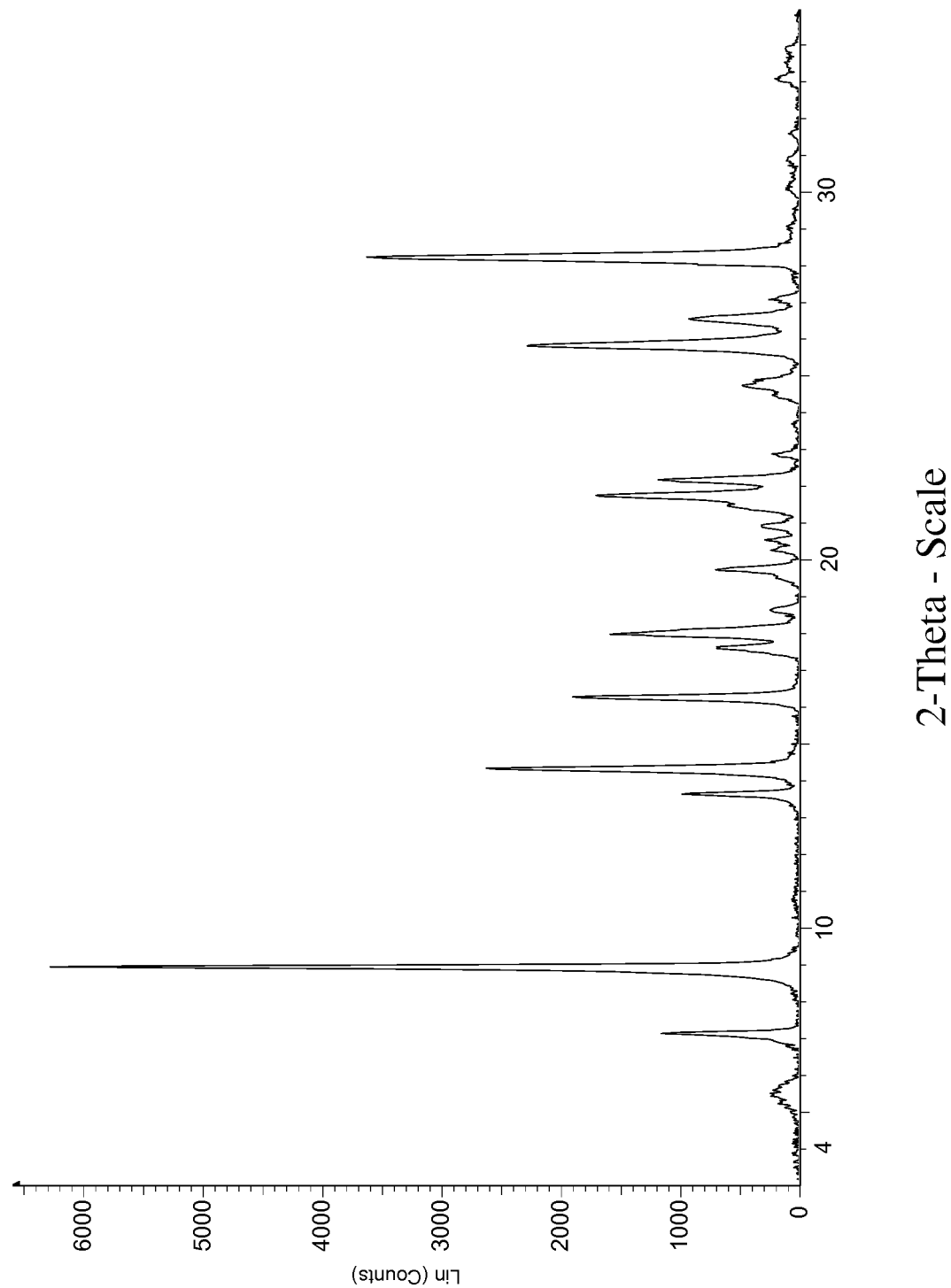
Fig. 3: XRPD Pattern for the 1:1 VR588 Gentisic Acid Cocrystal

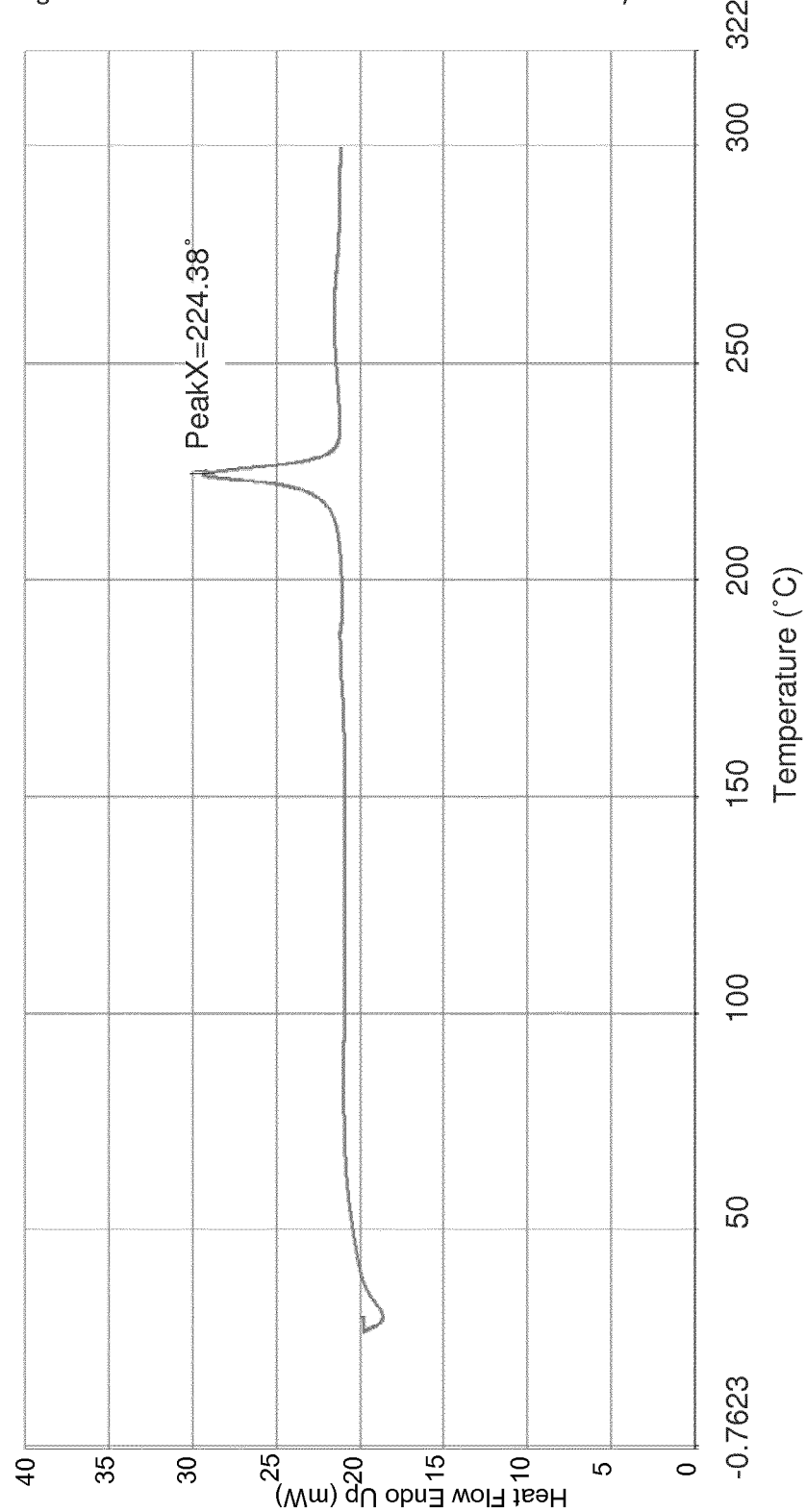

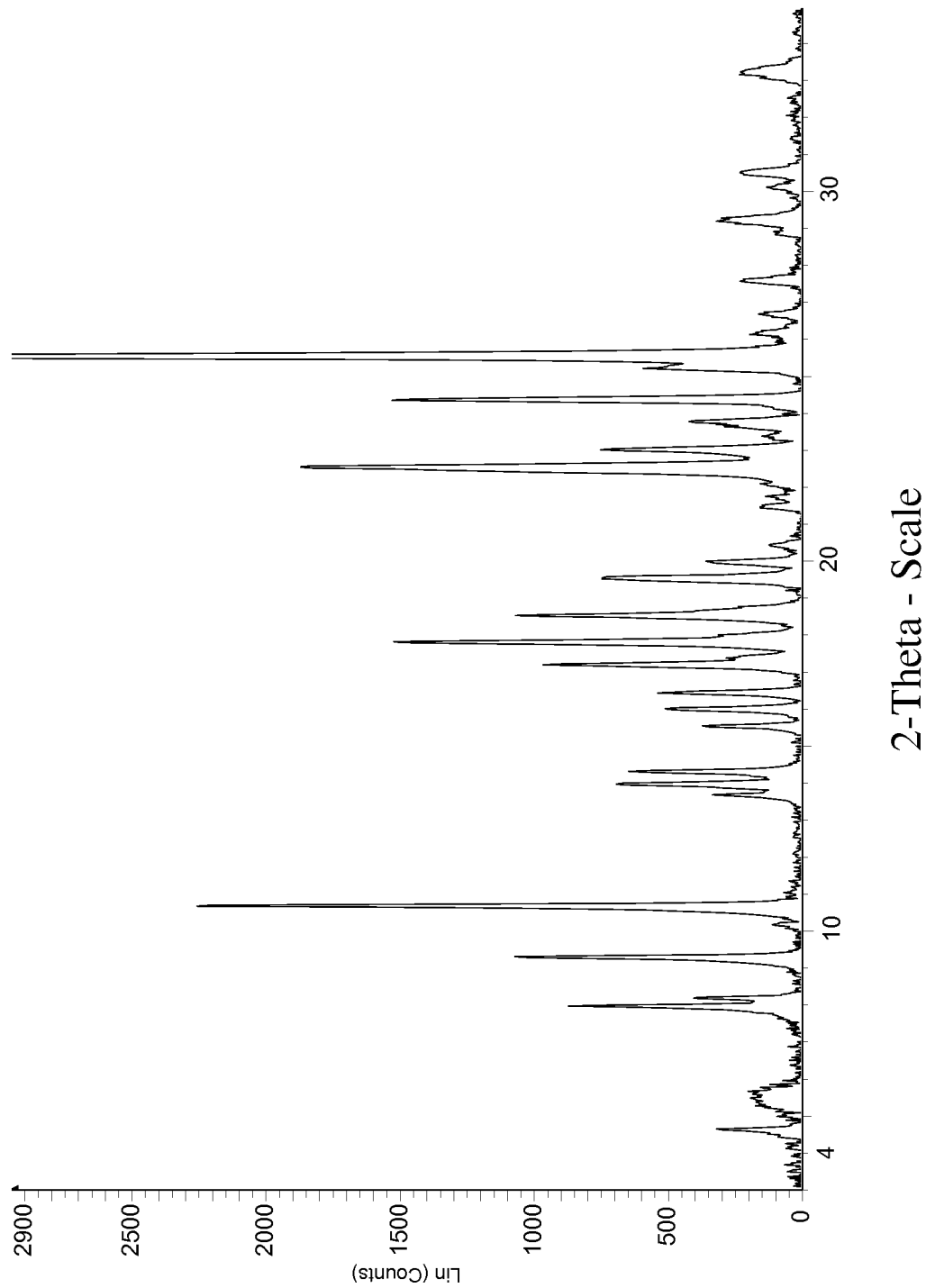
Fig. 5: XRPD Pattern for the 2:1 VR588 Adipic Acid Cocrystal

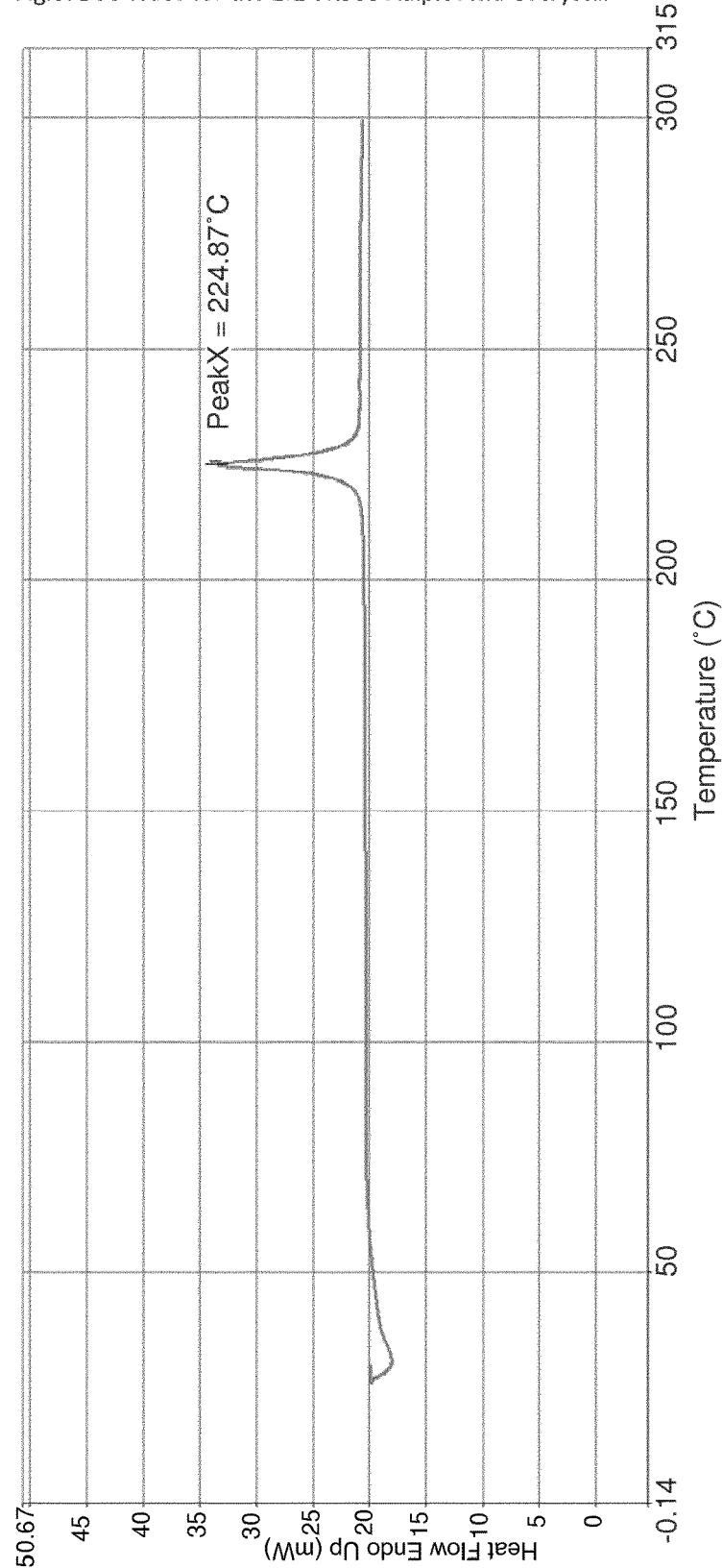
Fig.6: DSC Trace for the 2:1 VR588 Adipic Acid Cocrystal

CRYSTALLINE FORM OF A JAK3 KINASE INHIBITOR

This application is a national stage filing under 35 U.S.C. § 371 of International Application No. PCT/EP2016/054237, filed on Feb. 29, 2016, which claims priority of European Patent Application No. 15158443.0, filed Mar. 10, 2015. The contents of these applications are each incorporated herein by reference.

The present invention relates to new forms of pharmaceutical compounds, pharmaceutical compositions containing them and their use as therapeutic agents.

WO2011/051452 discloses compounds which are useful as Janus kinase inhibitors, in particular JAK3 inhibitors. The compounds disclosed therein have utility in the treatment of various diseases, including respiratory indications such as asthma and COPD.

Drugs for the treatment of respiratory diseases are frequently administered via dry powder inhalation devices. Formulating such drugs as dry powders with inhalation excipients such as lactose is often complicated and unpredictable. There is a need for stable dry powder formulations which exhibit desirable bioavailability and physical properties such as crystallinity, stability, density, flow characteristics and electrostatic charge such that an effective dose is delivered to the correct part of the lung.

Different techniques have been developed for different drug substances in an attempt to produce inhalation powders having the desired physiochemical properties. For example the drug substance may be produced as a pharmaceutical salt or polymorphic form, or may be developed as a specific formulation. Less frequently it may be possible to prepare a co-crystal of a drug substance. A co-crystal is a distinct chemical entity prepared from the drug substance and another chemical compound, the second compound being described as a co-former. The co-crystal possesses distinct crystallographic and spectroscopic properties as well as unique thermal properties. Examples can be found in WO2013/144916.

It has now surprisingly been found that a drug substance disclosed in WO2011/051452, namely the compound (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile having the structure shown below can be prepared as a stable co-crystal with certain co-formers.

Compound (I)

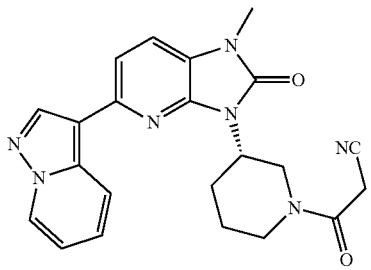

Therefore, in one embodiment the invention comprises a co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile. In one embodiment the invention comprises a 1:1 co-crystal. In a further embodiment the invention comprises a 2:1 co-crystal. In one embodiment the invention comprises a co-crystal formed with a compound selected from maleic acid, gentisic acid or adipic acid.

The co-crystals of the invention, in particular the maleic acid co-crystal, show good aerosol performance when compared to Compound (I) alone.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid having an X-ray powder diffraction pattern substantially as shown in FIG. 1.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid having an X-ray powder diffraction pattern which shows the following diffraction angles (2Theta) using copper Kα radiation:
at approximately 8.4°
at approximately 8.8°
at approximately 11.5°
at approximately 16.2°
at approximately 18.6°
at approximately 21.6°
at approximately 23.9°
at approximately 25.9°

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid having an X-ray powder diffraction pattern which shows the following diffraction angles (2Theta) using copper Kα radiation:
at 8.4°
at 8.8°
at 11.5°
at 16.2°
at 18.6°
at 21.6°
at 23.9°
at 25.9°

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid having a single endotherm with an onset temperature of 166.2° C. and a peak maximum of 181.4° C.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid having an X-ray powder diffraction pattern substantially as shown in FIG. 2.

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid having an X-ray powder diffraction pattern which shows the following diffraction angles (2Theta) using copper Kα radiation:
at approximately 7.1°
at approximately 8.9°
at approximately 14.3° at approximately 16.3°
at approximately 18.0°
at approximately 21.7°
at approximately 25.8°
at approximately 28.2°

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid having an X-ray powder diffraction pattern which shows the following diffraction angles (2Theta) using copper Kα radiation:
at 7.1°
at 8.9°
at 14.3°
at 16.3°
at 18.0°
at 21.7°
at 25.8°
at 28.2°

In one embodiment the invention comprises a 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid having a single endotherm with an onset temperature of 196.8° C. and a peak maximum of 224.4° C.

In one embodiment the invention comprises a 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid.

In one embodiment the invention comprises a 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid having an X-ray powder diffraction pattern substantially as shown in FIG. 3.

In one embodiment the invention comprises a 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid having an X-ray powder diffraction pattern which shows the following diffraction angles (2Theta) using copper Kα radiation:
at approximately 4.6°
at approximately 9.3°
at approximately 10.7°
at approximately 14.3°
at approximately 15.5°
at approximately 17.2°
at approximately 18.5°
at approximately 22.4°

In one embodiment the invention comprises a 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid having an X-ray powder diffraction pattern which shows the following diffraction angles (2Theta) using copper Kα radiation:
at 4.6°
at 9.3°
at 10.7°
at 14.3°
at 15.5°
at 17.2°
at 18.5°
at 22.4°

In one embodiment the invention comprises a 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid having a single endotherm with an onset temperature of 209.7° C. and a peak maximum of 224.9° C.

The co-crystals of the invention have been found to exhibit desirable physical properties and are therefore expected to be advantageous when formulated as dry powder compositions for inhalation, in particular for the treatment of respiratory indications. Particular diseases that may be treated with the co-crystals of the invention include asthma, COPD, pulmonary arterial hypertension (PAH), idiopathic pulmonary fibrosis (IPF) and lung cancer. In one embodiment the invention relates to the a co-crystal of Compound (I) as a therapeutic agent. In one embodiment the invention relates to the maleic acid co-crystal of Compound (I) as a therapeutic agent. In one embodiment the invention relates to the use of the maleic acid co-crystal of Compound (I) for the treatment of respiratory diseases.

In one embodiment the invention relates to use of the maleic acid co-crystal of Compound (I) for the treatment or prophylaxis of asthma or COPD, in particular severe asthma.

In a further embodiment the invention relates to a method of treatment of a respiratory disease which comprises administering to a patient in need thereof the maleic acid co-crystal of Compound (I), optionally in the presence of a pharmaceutical carrier or excipient.

In a further embodiment the invention relates to the use of the maleic acid co-crystal of Compound (I), in the manufacture of a medicament for treating respiratory diseases such as asthma or COPD, in particular severe asthma.

The co-crystals of the invention can be administered with one or more additional therapeutic agents, either simultaneously of sequentially. For respiratory indications the co-crystals of the invention can be administered in combination with a therapeutic agent or agents selected from inhaled corticosteroid, ß-agonists, long-acting muscarinic agonists, PDE4 inhibitors, or a biological agent such as an agent active at the IL-13, IL-5, IL-4/13, IL-17, IL-25 or IL-33 receptors. In particular the co-crystals of the invention can be administered with one or more compounds selected from salbutamol, glycopyrrolate, pirfenidone, nintedanib, beclomethasone, fluticasone, budesonide, mometasone, tiotropium, formoterol, indacaterol, vilanterol, umeclidinium and roflumilast.

In one embodiment the invention provides a co-crystal of Compound (I), in particular the maleic acid co-crystal of Compound (I). in combination with one or more additional therapeutic agents. In one embodiment the invention provides a co-crystal of Compound (I), in particular the maleic acid co-crystal of Compound (I), in combination with one or more compounds selected from salbutamol, glycopyrrolate, pirfenidone, nintedanib, beclomethasone, fluticasone, budesonide, mometasone, tiotropium, formoterol, indacaterol, vilanterol, umeclidinium and roflumilast.

The co-crystals of the invention are administered as pharmaceutical compositions, typically with a pharmaceutically excipient. Suitable compositions can be in the form of tablets, capsules, liquid suspensions, topical compositions, transdermal compositions or inhalable compositions. Solid dosage forms in which the crystalline form of the co-crystal is maintained are desirable and form a further embodiment of the invention. For the treatment of respiratory diseases inhalable compositions which can be delivered via a dry powder inhaler form a further embodiment of the invention.

For the treatment of respiratory diseases inhalable compositions which can be delivered via a dry powder inhaler (DPI) form a further embodiment of the invention. Compositions in the form of a suspension for delivery via a pressurised metered dose inhaler (pMDI) form a further aspect of the invention.

In one embodiment the invention relates to a pharmaceutical composition comprising a co-crystal of Compound (I) with one or more pharmaceutically acceptable excipients. In one embodiment the co-crystal is a 1:1 co-crystal of Compound (I) and maleic acid.

For administration by inhalation using a dry powder inhaler, the co-crystals of the invention can be administered as dry powder formulations with one or more carrier substances. Suitable inhalation carriers are known in the art and in one embodiment include crystalline sugars such as monosaccharides or disaccharides. In one preferred embodiment the carrier is lactose.

Dry powder formulations of the invention may also have additional excipients such as force control agents. A force control agent is an additive which reduces the cohesion between the fine particles within the powder formulation. This promotes de-agglomeration when the powder is dispensed from the inhaler. Suitable force control agents are known in the art. In one embodiment the force control agent is a metal stearate such as magnesium stearate. Typically about 1% w/w of magnesium stearate is added to a formulation of the invention.

The dry powder formulations of the invention are typically formulated to have a particle size for inhalation. In one embodiment the co-crystals of the invention are formulated to have an average particle size of less than about 10 μm, in one embodiment less than about 5 μm and in a further preferred embodiment in the range of about 1 μm to about 5 μm.

In one embodiment the maleic acid co-crystal is administered as a dry powder formulation with lactose, optionally magnesium stearate, with the formulation having an average particle size in the range of about 1 μm to about 5 μm.

The dry powder formulations of the invention can be administered using various dry powder inhalers such as GyroHaler® or a lever operated inhaler such as that disclosed in WO2009/092770. In a further embodiment the invention provides a kit comprising an inhaler in combination with a co-crystal of Compound (I) and one or more pharmaceutically acceptable excipients. In a further embodiment the invention provides a kit comprising a dry powder inhaler in combination with the maleic acid co-crystal of Compound (I) and one or more pharmaceutically acceptable excipients. In a further embodiment the invention provides a kit comprising a GyroHaler® dry powder inhaler in combination with the maleic acid co-crystal of Compound (I) and one or more pharmaceutically acceptable excipients. In a still further embodiment the invention provides a kit comprising a lever operated dry powder inhaler disclosed in WO 2009/092770 in combination with the maleic acid co-crystal of Compound (I) and one or more pharmaceutically acceptable excipients.

In a further embodiment the invention provides a kit comprising a dry powder inhaler in combination with the 1:1 maleic acid co-crystal of Compound (I) and one or more pharmaceutically acceptable excipients. In a still further embodiment the invention provides a kit comprising a GyroHaler® dry powder inhaler in combination with the 1:1 maleic acid co-crystal of Compound (I) and one or more pharmaceutically acceptable excipients.

The co-crystals of the invention can be prepared using methods known in the art, typically by mixing Compound (I) with a suitable co-former. The reaction is typically carried out in the presence of nitromethane. The resulting co-crystal is filtered and dried.

BRIEF DESCRIPTION OF THE DRAWINGS

FIG. 1 shows the XRPD pattern of the 1:1 VR588 maleic acid co-crystal.
FIG. 2. shows the differential scanning calorimetry (DSC) trace for the 1:1 VR588 maleic acid co-crystal.
FIG. 3. shows the XRPD pattern of the 1:1 VR588 gentisic acid co-crystal.
FIG. 4. shows the differential scanning calorimetry (DSC) trace for the 1:1 VR588 gentisic acid co-crystal.
FIG. 5. shows the XRPD pattern of the 1:1 VR588 adipic acid co-crystal.
FIG. 6. shows the differential scanning calorimetry (DSC) trace for the 1:1 VR588 adipic acid co-crystal.

EXAMPLES

The following examples illustrate the invention.
General Methodology
X-Ray Powder Diffraction Characterisation:
X-Ray Powder Diffraction patterns were collected on a PANalytical X'Pert PRO diffractometer using CuKα radiation (45 kV, 40 mA), θ-θ goniometer, focusing mirror (Cu W/Si), divergence slit (½°), soller slits at both incident and diffracted beam (0.04 RAD), fixed mask (4 mm) and a PIXcel detector. The software used for data collection was X'Pert Data Collector, version 2.2f. The instrument was performance checked using a certified Standard Reference Material® 640d, Silicon Powder (NIST). XRPD patterns were acquired under ambient conditions via a transmission foil sample stage (polyimide—Kapton®, TF-475, 7.5 μm thickness film). The specimen was examined as received with approximately 5 mg of the sample examined as dispensed onto the sample stage. The data collection range was 2.994-35.0056°2θ with a step size of 0.0263° and a continuous scan speed of $0.202004°s^{-1}$.

Thermal Analysis—Differential Scanning Calorimetry (DSC):

DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at $20°$ $C.·min^{-1}$ from 30 to 350° C. A purge of dry nitrogen at 60 ml·$min^{-1}$ was maintained over the sample. The instrument control, data acquisition and analysis were performed with Pyris Software v9.0.1.0203.

Example 1. 1:1 Maleic Acid Co-Crystal (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (100 mg) and maleic acid (28 mg) were weighed into a glass vial. Nitromethane (1.5 ml) was added to the vial, the vial was sealed and placed on a shaker for 24 hours. The product was filtered and dried in a vacuum oven (50° C.) overnight before being analysed by XRPD.

Larger Scale Method (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (2.00 g) and maleic acid (0.56 g) were placed in a round bottom flask. Nitromethane (40 ml) was added and the slurry was stirred for 24 hour at room temperature. The product was filtered and dried in a vacuum oven (50° C.) overnight before being analysed by XRPD.

1.2 XRPD Characterisation of a 1:1 Maleic Acid Co-Crystal

The experimental XRPD pattern of the 1:1 VR588 maleic acid co-crystal is shown in FIG. 1. Table 1 lists the angles, °2θ±0.2°2θ, and d-spacing of the peaks identified in the XRPD pattern of FIG. 1. The entire list of peaks, or a subset thereof, may be sufficient to characterise the co-crystal. For example, the co-crystal may be characterised by at least four peaks selected from the peaks at 8.4, 8.8, 11.5, 16.2, 18.6, 21.6, 23.9 and 25.9°2θ±0.2°2θ as well as by a XRPD pattern substantially similar to FIG. 1.

TABLE 1

| Angle °2θ ± 0.2 °2θ | d value Angstrom | Intensity % |
| --- | --- | --- |
| 7.8 | 11.40 | 18.40 |
| 8.4 | 10.54 | 56.50 |
| 8.8 | 10.02 | 100.00 |
| 11.5 | 7.71 | 62.70 |
| 14.9 | 5.95 | 10.10 |
| 15.6 | 5.67 | 8.30 |
| 16.2 | 5.47 | 27.90 |
| 16.9 | 5.25 | 19.80 |
| 17.4 | 5.09 | 27.70 |
| 17.9 | 4.96 | 30.60 |
| 18.6 | 4.75 | 25.40 |
| 19.4 | 4.57 | 8.40 |
| 19.9 | 4.45 | 12.30 |
| 20.2 | 4.40 | 8.40 |
| 21.0 | 4.22 | 12.30 |
| 21.3 | 4.17 | 11.90 |
| 21.6 | 4.11 | 25.00 |
| 22.6 | 3.93 | 8.30 |
| 22.9 | 3.87 | 22.30 |
| 23.3 | 3.81 | 35.10 |
| 23.9 | 3.72 | 45.40 |
| 24.4 | 3.65 | 7.70 |
| 24.8 | 3.58 | 12.90 |
| 25.1 | 3.55 | 9.30 |
| 25.9 | 3.44 | 58.90 |
| 26.4 | 3.37 | 11.20 |
| 27.1 | 3.29 | 15.60 |
| 27.6 | 3.23 | 21.30 |
| 28.9 | 3.08 | 10.90 |
| 30.0 | 2.98 | 11.30 |
| 30.7 | 2.91 | 6.10 |
| 31.1 | 2.88 | 6.40 |

1.3 DSC of 1:1 Maleic Acid Co-Crystal

The differential scanning calorimetry (DSC) trace, FIG. 2, shows a single endotherm with an onset temperature of 166.2° C. and a peak maximum of 181.4° C.

Example 2. 1:1 Gentisic Acid Co-Crystal (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (100 mg) and gentisic acid (37 mg) were weighed into a glass vial. Nitromethane (1.5 ml) was added to the vial, the vial was sealed and placed on a shaker for 24 hours. The product was filtered and dried in a vacuum oven (50° C.) overnight before being analysed by XRPD.

Larger Scale Method (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (3.00 g) and gentisic acid (1.11 g) were placed in a round bottom flask. Nitromethane (45 ml) was added and the slurry was stirred for 24 hour at room temperature. The product was filtered and dried in a vacuum oven (50° C.) overnight before being analysed by XRPD.

2.2 XRPD Characterisation of a 1:1 Gentisic Acid Co-Crystal

The experimental XRPD pattern of the 1:1 gentisic acid co-crystal is shown in FIG. 3. Table 2 lists the angles, °2θ±0.2°2θ, and d-spacing of the peaks identified in the XRPD pattern of FIG. 3. The entire list of peaks, or a subset thereof, may be sufficient to characterise the co-crystal. For example, the co-crystal may be characterised by at least four peaks selected from the peaks at 7.1, 8.9, 14.3, 16.3, 18.0, 21.7, 25.8 and 28.2°2θ±0.2°2θ as well as by a XRPD pattern substantially similar to FIG. 3.

TABLE 2

| Angle °2θ ± 0.2 °2θ | d value Angstrom | Intensity % |
| --- | --- | --- |
| 7.1 | 12.5 | 23.3 |
| 8.9 | 9.9 | 100.0 |
| 13.6 | 6.5 | 18.4 |
| 14.3 | 6.2 | 43.3 |
| 16.3 | 5.4 | 32.3 |
| 17.6 | 5.0 | 14.1 |
| 18.0 | 4.9 | 27.7 |
| 18.7 | 4.8 | 7.3 |
| 19.8 | 4.5 | 14.4 |
| 20.3 | 4.4 | 7.4 |
| 20.6 | 4.3 | 8.2 |
| 20.9 | 4.2 | 8.6 |
| 21.5 | 4.1 | 12.8 |
| 21.7 | 4.1 | 29.5 |
| 22.2 | 4.0 | 21.5 |
| 22.9 | 3.9 | 6.6 |
| 24.5 | 3.6 | 6.5 |
| 24.7 | 3.6 | 10.5 |
| 25.8 | 3.4 | 38.1 |
| 26.6 | 3.4 | 17.6 |
| 27.1 | 3.3 | 7.4 |
| 28.2 | 3.2 | 58.2 |

2.3 DSC of 1:1 Gentisic Acid Co-Crystal

The differential scanning calorimetry (DSC) trace, FIG. 4, shows a single endotherm with an onset temperature of 196.8° C. and a peak maximum of 224.4° C.

Example 3. 2:1 Adipic Acid Co-Crystal (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (100 mg) and adipic acid (18 mg) were weighed into a glass vial. Nitromethane (1.5 ml) was added to the vial, the vial was sealed and placed on a shaker for 24 hours. The product was filtered and dried in a vacuum oven (50° C.) overnight before being analysed by XRPD.

Larger Scale Method (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (3.00 g) and adipic acid (0.53 g) were placed in a round bottom flask. Nitromethane (45 ml) was added and the slurry was stirred for 24 hour at room temperature. The product was filtered and dried in a vacuum oven (50° C.) overnight before being analysed by XRPD.

3.2 XRPD Characterisation of a 2:1 Adipic Acid Co-Crystal

The experimental XRPD pattern of the 2:1 adipic acid co-crystal is shown in FIG. 5. Table 3 lists the angles, °2θ±0.2°2θ, and d-spacing of the peaks identified in the XRPD pattern of FIG. 5. The entire list of peaks, or a subset thereof, may be sufficient to characterise the co-crystal. For example, the co-crystal may be characterised by at least four peaks selected from the peaks at 4.6, 9.3, 10.7, 14.3, 15.5, 17.2, 18.5 and 22.4°2θ±0.2°2θ as well as by a XRPD pattern substantially similar to FIG. 5.

TABLE 3

| Angle 2-Theta° | d value Angstrom | Intensity % |
|---|---|---|
| 4.6 | 19.3 | 7.7 |
| 7.9 | 11.2 | 21.1 |
| 8.2 | 10.8 | 9.8 |
| 9.3 | 9.5 | 26.1 |
| 10.7 | 8.3 | 55.0 |
| 13.6 | 6.5 | 8.1 |
| 13.9 | 6.3 | 16.8 |
| 14.3 | 6.2 | 15.7 |
| 15.5 | 5.7 | 8.9 |
| 16.0 | 5.5 | 12.4 |
| 16.4 | 5.4 | 13.0 |
| 17.2 | 5.2 | 23.5 |
| 17.8 | 5.0 | 37.1 |
| 18.5 | 4.8 | 26.0 |
| 19.5 | 4.5 | 18.1 |
| 20.0 | 4.4 | 8.6 |
| 22.5 | 3.9 | 45.6 |
| 23.0 | 3.9 | 18.2 |
| 23.8 | 3.7 | 10.2 |
| 24.4 | 3.6 | 37.2 |
| 25.2 | 3.5 | 14.4 |
| 25.5 | 3.5 | 100.0 |
| 27.6 | 3.23 | 5.50 |
| 29.2 | 3.05 | 7.70 |
| 30.5 | 2.93 | 5.50 |
| 33.2 | 2.69 | 5.50 |

3.3 DSC of 2:1 Adipic Acid Co-Crystal

The differential scanning calorimetry (DSC) trace, FIG. 6, shows a single endotherm with an onset temperature of 209.7° C. and a peak maximum of 224.9° C.

4. Fine Particle Fraction Data

Co-crystals of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (Compound 1) were prepared according to the examples 1-3 above.

The aerodynamic particle size distribution (APSD) of the formulations was evaluated with the Next Generation Impactor (NGI) tested at a flow rate of 80 Lmin$^{-1}$ in the GyroHaler® device (Compound 1—Gentisic Acid) and 60 Lmin$^{-1}$ in the F1 device (Compound 1, Compound 1—Maleic Acid and Compound 1—Adipic Acid). One dose was collected for each NGI measurement. Compound 1 deposition on the NGI components was measured by a gradient high performance liquid Chromatography (HPLC) method with UV detection.

The co-crystals with adipic acid and maleic acid were tested in a Vectura unit dose device as disclosed in WO2010/086285, and the gentisic acid co-crystal was tested in a GyroHaler® device. All three co-crystals exhibited good fine particle mass data and associated stability as shown in the table below, with the maleic acid co-crystal being particularly advantageous.

| | Fine particle Mass (μg < 5 μm) - 1000 μg dose load in 20 mg formulation | | |
|---|---|---|---|
| Crystal | T = 0 w | T = 4 w | T = 12 w |
| Compound 1 | 418.2 | 450.7 | 415.3 |
| Compound 1: Maleic Acid | 412.4 | 396.4 | 469.6 |
| Compound 1: Adipic Acid | 349.1 | 296.6 | 261.0 |
| Compound 1: Gentisic Acid | 378.8 | 309.3 | 310.6 |

The invention claimed is:

1. A co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile.

2. A 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with maleic acid.

3. A co-crystal according to claim 2 having an X-ray powder diffraction pattern which shows the following diffraction angles (2Theta) using copper Kα radiation:
at approximately 8.4°;
at approximately 8.8°;
at approximately 11.5°;
at approximately 16.2°;
at approximately 18.6°;
at approximately 21.6°;
at approximately 23.9°; and
at approximately 25.9°.

4. A co-crystal according to claim 3 having a single endotherm with an onset temperature of 166.2° C. and a peak maximum of 181.4° C.

5. A 1:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with gentisic acid.

6. A co-crystal according to claim 4 having an X-ray powder diffraction pattern which shows the following diffraction angles (2Theta) using copper Kα radiation:
at approximately 7.1°;
at approximately 8.9°;
at approximately 14.3°;
at approximately 16.3°;
at approximately 18.0°;
at approximately 21.7°;
at approximately 25.8°; and
at approximately 28.2°.

7. A 2:1 co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with adipic acid.

8. A co-crystal according to claim 6 having an X-ray powder diffraction pattern which shows the following diffraction angles (2Theta) using copper Kα radiation:
at approximately 4.6°;
at approximately 9.3°;
at approximately 10.7°;
at approximately 14.3°;
at approximately 15.5°;
at approximately 17.2°;
at approximately 18.5°; and
at approximately 22.4°.

9. A pharmaceutical composition comprising a co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile and a pharmaceutically acceptable carrier or excipient.

10. The composition according to claim 9 wherein the co-crystal is a 1:1 co-crystal with maleic acid.

11. A method of treating asthma or chronic obstructive pulmonary disease (COPD) comprising administering to a patient in need thereof a maleic acid co-crystal of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile.

12. The method according to claim 11 in which the co-crystal is a 1:1 co-crystal with maleic acid.

13. The method according to claim 11 wherein treating the disease is an acute or prophylactic treatment.

\* \* \* \* \*